US00PP17400P2

(12) United States Plant Patent
Oudshoorn

(10) Patent No.: US PP17,400 P2
(45) Date of Patent: Feb. 6, 2007

(54) ***ASTER* PLANT NAMED 'OUDSHOORN 1'**

(50) Latin Name: *Aster hybrida*
Varietal Denomination: Oudshoorn 1

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 18 days.

(21) Appl. No.: 11/151,788

(22) Filed: Jun. 14, 2005

(51) Int. Cl.
*A01H 5/00* (2006.01)

(52) U.S. Cl. ..... Plt./355
(58) Field of Classification Search ..... Plt./355
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of cut flower *Aster* plant named 'Oudshoorn 1', characterized by its strong flowering stems; freely flowering habit; long flowering period; daisy-type inflorescences with violet-colored ray florets; long and straight ray florets; and good garden performance.

1 Drawing Sheet

Botanical designation: *Aster hybrida.*
Cultivar denomination: 'Oudshoorn 1'.

BACKGROUND OF THE INVENTION

The present Invention relates to a new and distinct cultivar of cut flower *Aster* plant, botanically known as *Aster hybrida* and hereinafter referred to by the name 'Oudshoorn 1'.

The new *Aster* is a product of a planned breeding program conducted by the Inventor in Rijpwetering, The Netherlands. The objective of the breeding program is to create new *Aster* cultivars with durable leaves and attractive floret colors.

The new *Aster* originated from a chance cross-pollination in Rijpwetering, The Netherlands, of an unnamed *Aster* selection, not patented, as the female, or seed, parent with an unknown *Aster* selection as the male, or pollen, parent. The new *Aster* was discovered and selected by the Inventor as a single flowering plant within the progeny of the stated cross-pollination grown in a controlled environment in Rijpwetering, The Netherlands in 1999.

Asexual reproduction of the new *Aster* by vegetative tip cuttings was first conducted in Rijpwetering, The Netherlands in 2001. Asexual reproduction by cuttings has shown that the unique features of this new *Aster* are stable and reproduced true to type in successive generations.

SUMMARY OF THE INVENTION

The cultivar Oudshoorn 1 has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Oudshoorn 1'. These characteristics in combination distinguish 'Oudshoorn 1' as a new and distinct cut flower *Aster:*

1. Strong flowering stems.
2. Freely flowering habit.
3. Long flowering period.

4. Daisy-type inflorescences with violet-colored ray florets.
5. Long and straight ray florets.
6. Good garden performance.

Plants of the new *Aster* can be compared to plants of the female parent selection. Plants of the new *Aster* differ primarily from plants of the female parent selection in ray floret coloration.

Plants of the new *Aster* can be compared to plants of the cultivar Professor Anton Kippenberg, not patented. In side-by-side comparisons conducted in Rijpwetering, The Netherlands, plants of the new *Aster* were stronger and healthier than plants of the cultivar Professor Anton Kippenberg.

BRIEF DESCRIPTION OF THE PHOTOGRAPHS

The accompanying colored photographs illustrate the overall appearance of the new *Aster* showing the colors as true as it is reasonably possible to obtain in colored reproductions of this type. Colors in the photographs may differ from the color values cited in the detailed botanical description which accurately describe the colors of the new *Aster.*

The photograph at the top of the sheet comprises a side perspective view of a typical flowering stem of 'Oudshoorn 1'.

The photograph in the middle of the sheet is a close-up view of a typical inflorescence of 'Oudshoorn 1'.

The photograph at the bottom of the sheet is a close-up view of the upper surface of a typical leaf of 'Oudshoorn 1'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown and flowered during the summer and fall in Rijpwetering, The Netherlands in an outdoor nursery and under conditions which approximate those generally used in commercial *Aster* production. During the production of these plants, day temperatures ranged from 14 to 32° C. and night temperatures ranged from 4 to 16° C. Plants were about one year from planting rooted young plants when the photographs and the botanical description were taken.

Botanical classification: *Aster hybrida* cultivar Oudshoorn 1.

Parentage:

*Female, or seed, parent.*—Unnamed *Aster hybrida* selection, not patented.

*Male, or pollen, parent.*—Unknown *Aster hybrida* selection, not patented.

Propagation:

*Type.*—Terminal vegetative cuttings.

*Time to produce a rooted young plant.*—About three months at 18° C.

*Root description.*—Fine, fibrous; light brownish white in color.

*Rooting habit.*—Freely branching.

Plant description:

*Appearance.*—Herbaceous daisy-type *Aster*. Flowering stems upright and strong; inverted triangle. Moderately vigorous.

*Plant height.*—About 26.3 cm.

*Plant width.*—About 15.5 cm.

*Lateral branches.*—Quantity per plant: About eight. Length: About 16.7 cm. Diameter: About 2 mm. Internode length: About 2.5 cm. Strength: Strong. Texture: Pubescent. Color, young stems: 138A to 138B. Color, mature stems: 200B.

*Foliage description.*—Arrangement: Alternate, simple; sessile. Length: About 6.2 cm. Width: About 1.5 cm. Shape: Oblanceolate. Apex: Broadly acute. Base: Acuminate. Margin: Entire. Texture, upper and lower surfaces: Pubescent. Color: Developing foliage, upper surface: Between 141A and 143A. Developing foliage, lower surface: 143A. Fully expanded foliage, upper surface: 137B. Fully expanded foliage, lower surface: 137C. Venation, upper and lower surfaces: 138B.

Inflorescence description:

*Appearance.*—Daisy-type inflorescence form with narrowly ligulate-shaped ray florets. Inflorescences terminal or axillary. Disk and ray florets develop acropetally on a capitulum. Inflorescences persistent. Inflorescences face mostly upright. Uniform and freely flowering habit.

*Flowering response.*—Plants flower from early September to mid-October in The Netherlands; flowering continuous during this period.

*Postproduction longevity.*—Inflorescences maintain good color and substance for about four weeks on the plant.

*Quantity of inflorescences.*—About 16 inflorescences develop per plant.

*Fragrance.*—Moderate; sweet.

*Inflorescence bud.*—Height: About 1.6 cm. Diameter: About 8 mm. Shape: Ovate. Color: 143A to 144A.

*Inflorescence size.*—Diameter: About 4.6 cm. Depth (height): About 2.6 cm. Diameter of disc: About 1.1 cm. Receptacle diameter: About 8 mm. Receptacle height: About 1 cm.

*Ray florets.*—Number of ray florets per inflorescence/arrangement: About 27 in arranged in a single whorl. Length: About 2.7 cm. Width: About 3 mm. Shape: Narrowly ligulate. Apex: Obtuse. Base: Cuneate Margin: Entire. Texture, upper and lower surfaces: Smooth, glabrous. Orientation: Initially upright, then horizontal. Aspect: Mostly straight. Color: When opening, upper surface: N87A; towards the base, N88B. When opening, lower surface: N87C. Fully opened, upper surface: N87A. Fully opened, lower surface: N87B.

*Disc florets.*—Arrangement: Massed at center of receptacle. Number of disc florets per inflorescence: About 30. Length: About 1.2 cm. Diameter, apex: About 3 mm. Diameter, base: About 1.5 mm. Shape: Tubular. Apex: Five lobes; lobes acute. Color, immature: 150B. Color, mature: 145D.

*Phyllaries.*—Quantity per inflorescence: About 16. Length: About 7 mm. Width: About 2.5 mm. Shape: Narrowly oblong. Apex: Acute. Base: Cuneate. Texture, upper and lower surfaces: Pubescent. Color, upper surface: 143A to 143B. Color, lower surface: 143A.

*Peduncles.*—Length, terminal peduncle: About 6.8 cm. Diameter: About 1.5 mm. Aspect: Erect to about 20° from vertical. Strength: Strong. Texture: Pubescent. Color: 138A to 138B to 200B.

*Reproductive organs.*—Androecium: Present on disc florets only. Quantity of stamens per disc floret: Two. Anther shape: Linear. Anther length: About 2 mm. Anther color: 14B. Filament color: 145C to 145D. Pollen amount: Scarce. Pollen color: 14B. Gynoecium: Present on both ray and disc florets. Quantity per floret: One. Pistil length: About 6.5 mm. Stigma shape: Cleft. Stigma color: 12A. Style length: About 4.5 mm. Style color: 1B to 1C. Ovary color: 145C.

*Seed.*—Seed development has not been observed.

Disease/pest resistance: Resistance to pathogens and pests common to *Asters* has not been observed on plants grown under commercial greenhouse conditions.

Garden performance: Plants of the new *Aster* have been observed to have good garden performance and to tolerate wind and rain. Plants of the new *Aster* have been observed to be hardy to USDA Zone 5 and to tolerate temperatures to about 35° C.

It is claimed:

1. A new and distinct cultivar of cut flower *Aster* plant named 'Oudshoorn 1', as illustrated and described.

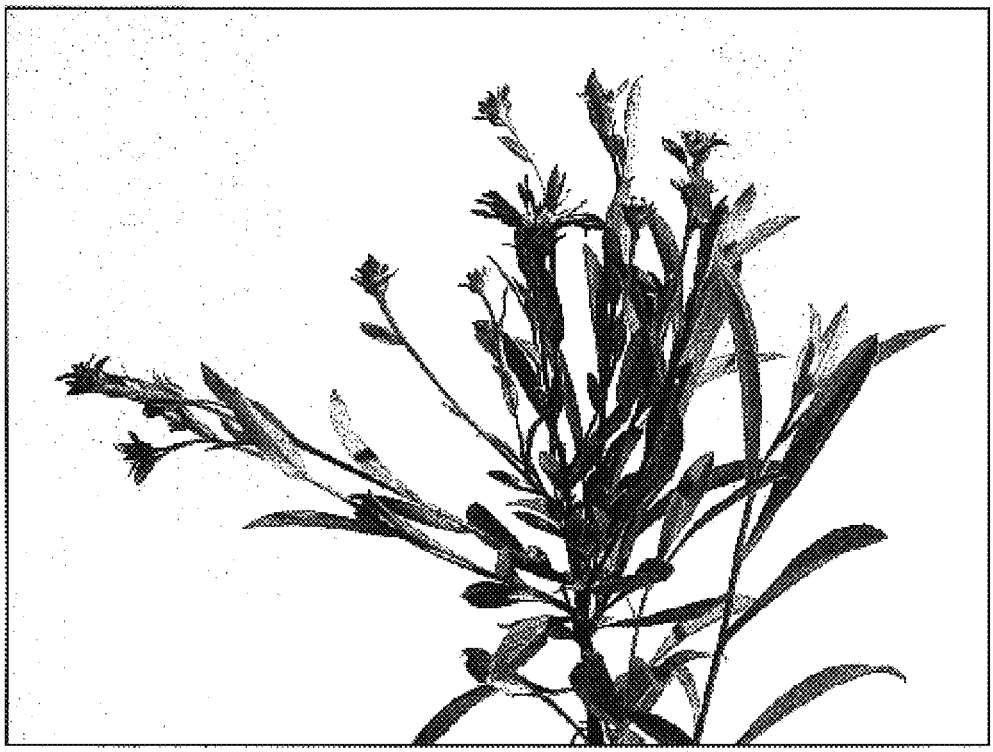
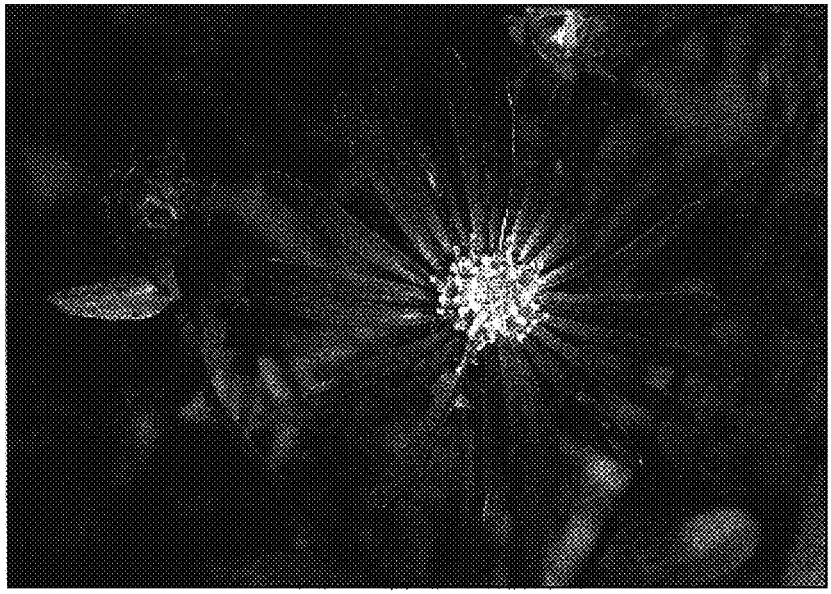
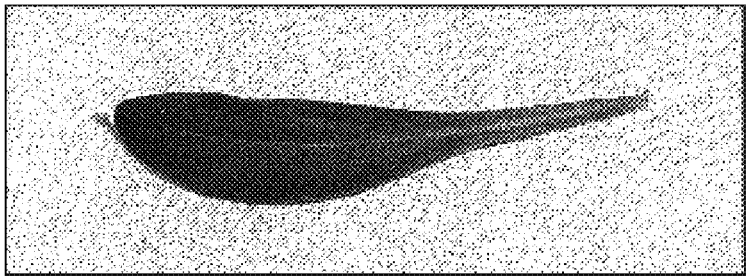

* * * * *